United States Patent
Haney et al.

(10) Patent No.: US 7,249,789 B2
(45) Date of Patent: Jul. 31, 2007

(54) WATER WELL CASING

(75) Inventors: Morris G. Haney, Beeville, TX (US); Roy L. Thein, Oklahoma City, OK (US)

(73) Assignee: Johnson Screens, Inc., Houston, TX (US)

( * ) Notice: Subject to any disclaimer, the term of this patent is extended or adjusted under 35 U.S.C. 154(b) by 0 days.

(21) Appl. No.: 10/965,108

(22) Filed: Oct. 14, 2004

(65) Prior Publication Data

US 2006/0082153 A1  Apr. 20, 2006

(51) Int. Cl.
*F16L 21/02* (2006.01)

(52) U.S. Cl. .................. 285/374; 285/330; 285/332.3; 285/347; 285/322; 285/921; 138/109

(58) Field of Classification Search .............. 285/330, 285/331, 332.1, 332.2, 332.3, 347, 921, 319, 285/374, 322; 405/251
See application file for complete search history.

(56) References Cited

U.S. PATENT DOCUMENTS

| | | | | |
|---|---|---|---|---|
| 1,039,354 A * | 9/1912 | Bonadio | ...................... | 285/276 |
| 1,678,280 A * | 7/1928 | Carson | ...................... | 285/332 |
| 2,537,284 A * | 1/1951 | Schuder | ...................... | 285/319 |
| 3,413,021 A | 11/1968 | Potts | | |
| 3,784,235 A | 1/1974 | Kessler | | |
| 4,030,850 A * | 6/1977 | Hyde | ...................... | 403/288 |
| 4,128,264 A | 12/1978 | Oldford | | |
| 4,486,034 A * | 12/1984 | Sauer | ...................... | 285/242 |
| 4,523,780 A * | 6/1985 | Cheer | ...................... | 285/399 |
| 4,552,387 A * | 11/1985 | Schmidt | ...................... | 285/238 |
| 4,779,902 A * | 10/1988 | Lee | ...................... | 285/260 |
| 4,803,053 A * | 2/1989 | Williamson | ................. | 422/101 |
| 4,875,714 A * | 10/1989 | Lee | ...................... | 285/86 |
| 4,887,849 A | 12/1989 | Briet | | |
| 5,015,014 A * | 5/1991 | Sweeney | ...................... | 285/81 |
| 5,255,945 A * | 10/1993 | Toon | ...................... | 285/305 |
| 5,662,360 A * | 9/1997 | Guzowski | ................... | 285/110 |
| 5,918,914 A | 7/1999 | Morris | | |
| 6,176,523 B1 * | 1/2001 | Winslett | ...................... | 285/24 |
| 6,499,772 B1 * | 12/2002 | Minemyer | ................. | 285/322 |
| 6,568,658 B2 * | 5/2003 | Strome | ...................... | 256/65.14 |

* cited by examiner

*Primary Examiner*—James M. Hewitt
(74) *Attorney, Agent, or Firm*—Gunn & Lee, P.C.

(57) ABSTRACT

A novel design for the connection of polyvinyl chloride (PVC) casing. Each length of casing has a male end and a female end. The female end has a narrowing interior diameter with its wider interior diameter at its outermost end sufficient to receive the male end of similar length of casing for connection. The diameter of the female end narrows to a diameter which is less than the outer diameter of the male end. The male end has a lip at its leading edge and is slotted and compressible when forced through the narrowed diameter of the female end. A groove in the interior surface of the female end is sufficient to receive the lip at the leading edge of the male end. When the lip at the leading edge of the male end reaches the groove, it allows the compressed male end to expand with the groove receiving the lip therein. The connected lengths of casing are locked together in this manner.

14 Claims, 5 Drawing Sheets

WATER WELL CASING

BACKGROUND OF THE INVENTION

1. Field of the Invention

Applicant's invention relates to a novel design for water well casing for use in water well and related systems.

2. Background Information

In water well systems, a casing is inserted into the well to maintain the structure of the well. Typically, a submersible pump is placed within the well and is attached a drop pipe which carries the water from the well to the surface. Since water well casing must extend many feet into the ground, it is advantageous to manufacture the casing in sections to facilitate installation as well as repair. Generally these sections are held together with glue or a pipe coupling. Unfortunately, the positioning of couplings can take a great deal of effort to assemble properly and the use of glue is time-consuming as glue requires a "set" time. Therefore, with current practices and materials, well drillers do not have the ability to run the casing into the well by simply and rapidly connecting one section of casing to another.

The present invention was designed to solve this problem. In the preferred embodiment, water well casing sections are provided having both male and female ends. The male end of one length of casing section fits within the female end of another length of casing. The male end is slotted and compressible when forced into the female end. The male end provides a lip which locks into a groove in the interior surface of the female end when the male end is fully inserted. The procedure allows the water well casing to be connected easily and efficiently without the use of glue or couplings.

A patent issued to Potts, U.S. Pat. No. 3,413,021, discloses a similar design for metal tubular couplings. Unlike the present invention, Potts discloses a coupling which is resistant to compressive forces and can be disassembled easily when pulled apart. On the other hand, the present invention is designed to resist the pulling or hanging loads which exist when the casing is placed in the well.

A patent issued to Oldford, U.S. Pat. No. 4,128,264 also has similarities to the present invention. However, the Oldford patent discloses a design for metal fittings to be used with metal pipe as opposed to plastic PVC casing disclosed in the present invention.

The prior art is devoid of any similar designs to be used with plastic piping or casing in water well applications.

SUMMARY OF THE INVENTION

It is an object of the present invention to provide novel water well casing that permits installation and connection without the use of glue or couplings. In satisfaction of these and related objectives, Applicant's present invention provides water well casing having a main length between male and female ends. The main length of the casing has a uniform inner and outer diameter and is contiguous with the male and female ends.

The male end has slots which are spaced around the circumference of the casing. The slots extend from the leading edge of the male end in a direction parallel to the length of the casing. The male end also has a lip at its leading edge. The lip is beveled at its front edge and forms a shoulder at its rear edge.

The female end has a first female section with a widened interior diameter at its outermost end designed to receive a male end of a similar length of casing. The interior diameter of the female end tapers and narrows to another section having a diameter which is less than outer diameter of the lip at the male end. A groove in interior surface of the female end is designed to receive and hold the lip of a similar length of casing.

During installation, the male end of one length of casing compresses as it is forced through the tapered diameter of the female end of another length of casing. Once the lip at the leading edge of the male end reaches the groove, the male end expands with the groove receiving and locking the lip therein.

DETAILED DESCRIPTION OF THE PREFERRED EMBODIMENT

Figure 1:
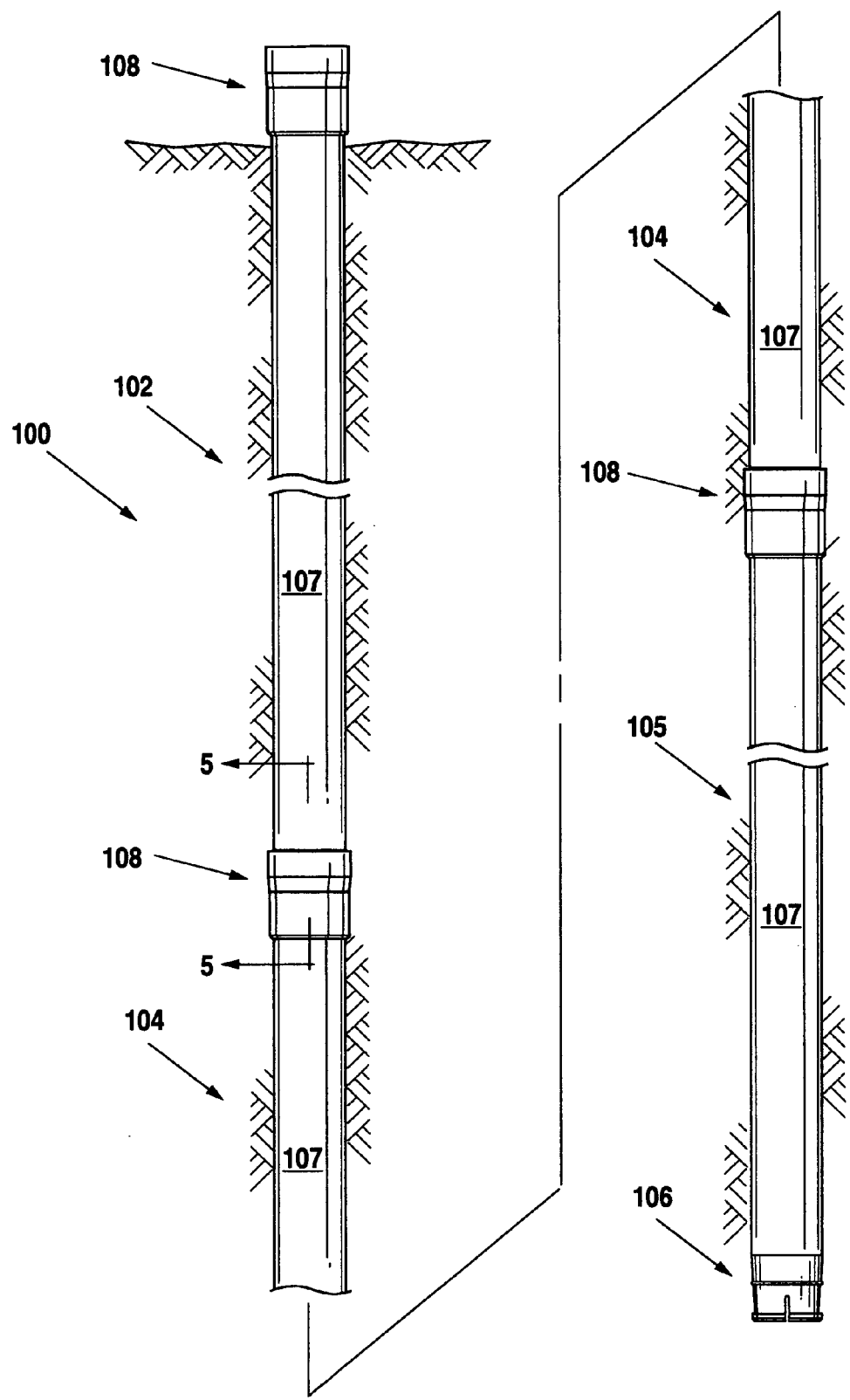
FIG. 1 is a front elevation view of a typical water well casing assembly.

FIG. 1 depicts a water well 100 with casing 102 placed in the water well 100 to maintain the integrity of the well 100 and protect pipe (not shown) within the casing 102. The casing 102 is present in separate similar lengths of casing 104 and 105 and connected one to the next by way of male ends 106 and female ends 108 shown in more detail in FIGS. 2, 3, and 4.

Referring to FIGS. 1, 2, 3, and 4, the casing 102 of the present invention consists of three parts, a main length 107, a male end 106 and a female end 108. In the preferred embodiment, the male end 106 has a tapering section 110 extending from the main length 107 to a lip 112 at the leading edge of the male end 106. The outer diameter of the lip 112 is substantially equal to the outer diameter of the main length 107. However, other designs of the male end are anticipated. For example, the outer diameter at the male end 106 could be uniform and equal to the outer diameter of the main length 107 with the lip 112 having an outer diameter greater than that of the main length 107. In another example, the male end 106 could have a uniform diameter which is narrower than the diameter of the main length.

Preferably, the interior diameter of the male end 106 is equal to the interior diameter of the main length 107. However, it is anticipated that the interior diameter of the male end 106 could be greater or less than the interior diameter of the main length 107.

In the preferred embodiment, the lip 112 has a beveled leading edge 120 and a squared shoulder 121 at its rear edge. However, it is anticipated that other designs for the lip could be utilized. For example, the leading edge of the lip 112 could be squared or rounded and the rear edge of the lip 112 could be curved or angled rearwardly.

The male end 106 has slots 122, which are spaced around the circumference of the male end 106 and extend from the lip 112 into the tapering section 110 in a direction substantially parallel to the length of the casing 102. Preferably, there are a plurality of slots 122 equally spaced around the circumference of the male end 106. However, it is anticipated that as few as one slot or a plurality of nonequally spaced slots could be utilized.

Figure 2:
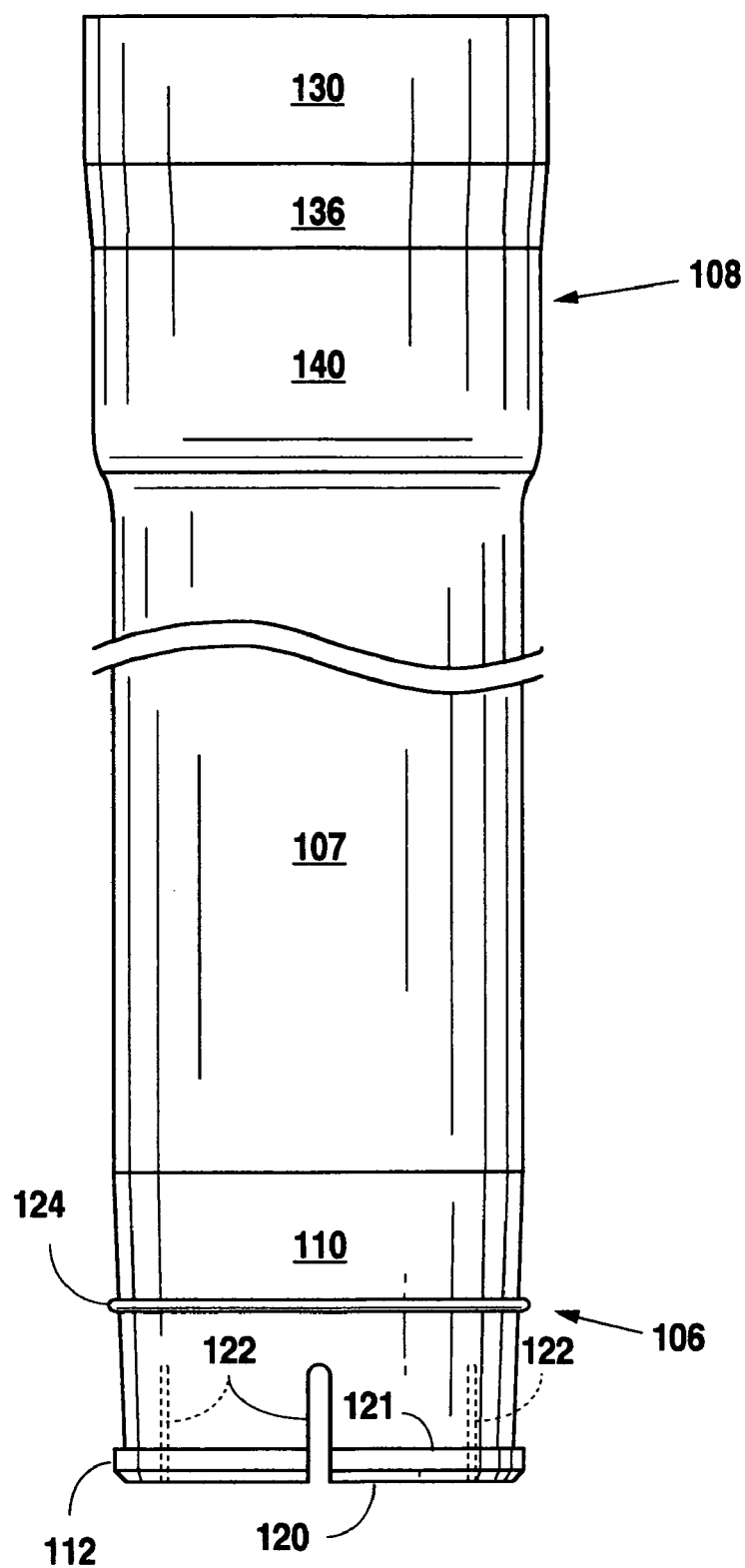
FIG. 2 is a side view of a length of the water well casing of the present invention casing showing the male and female ends.
Figure 3:
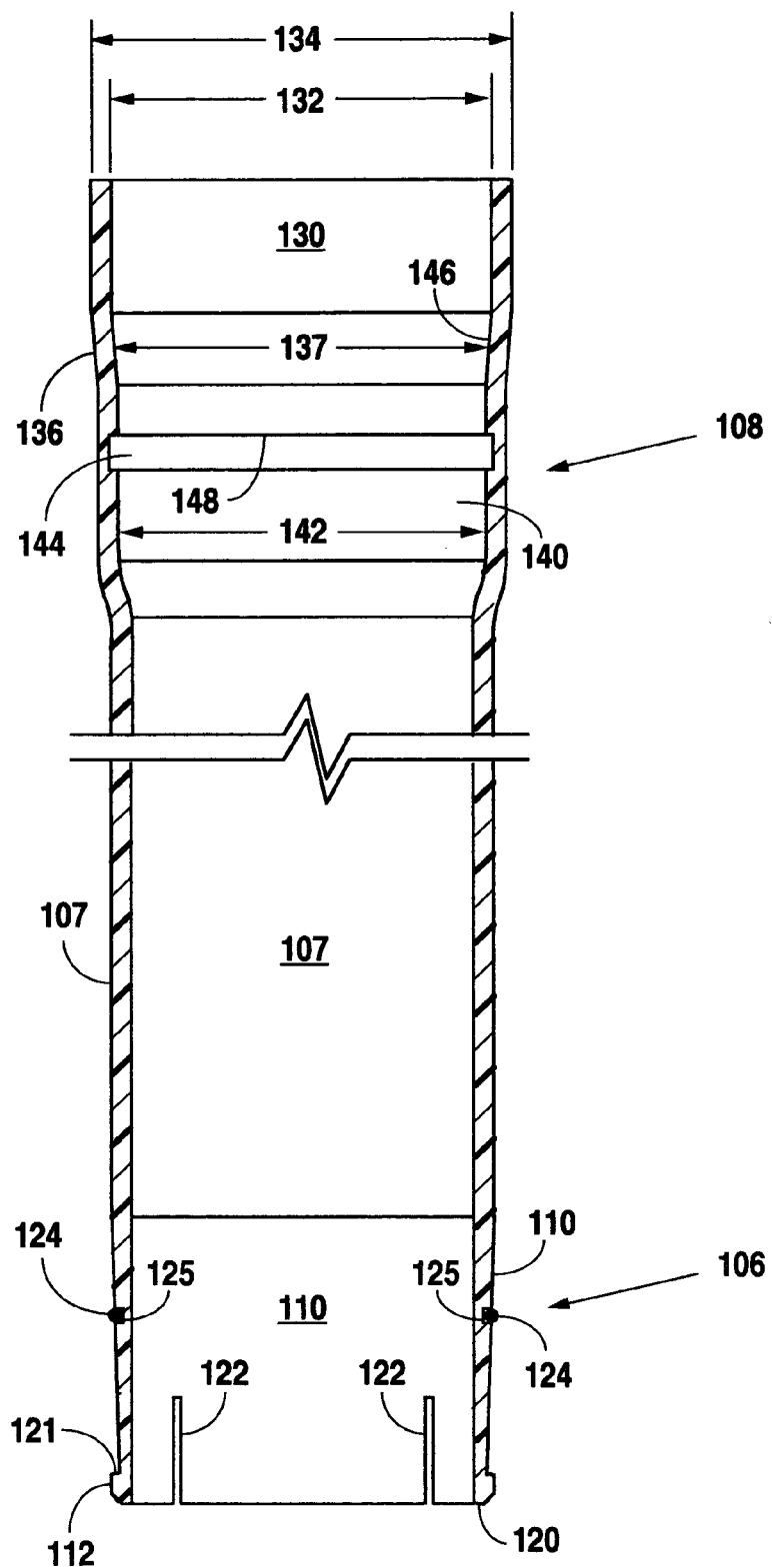
FIG. 3 is a cross-section view of FIG. 2.
Figure 4:
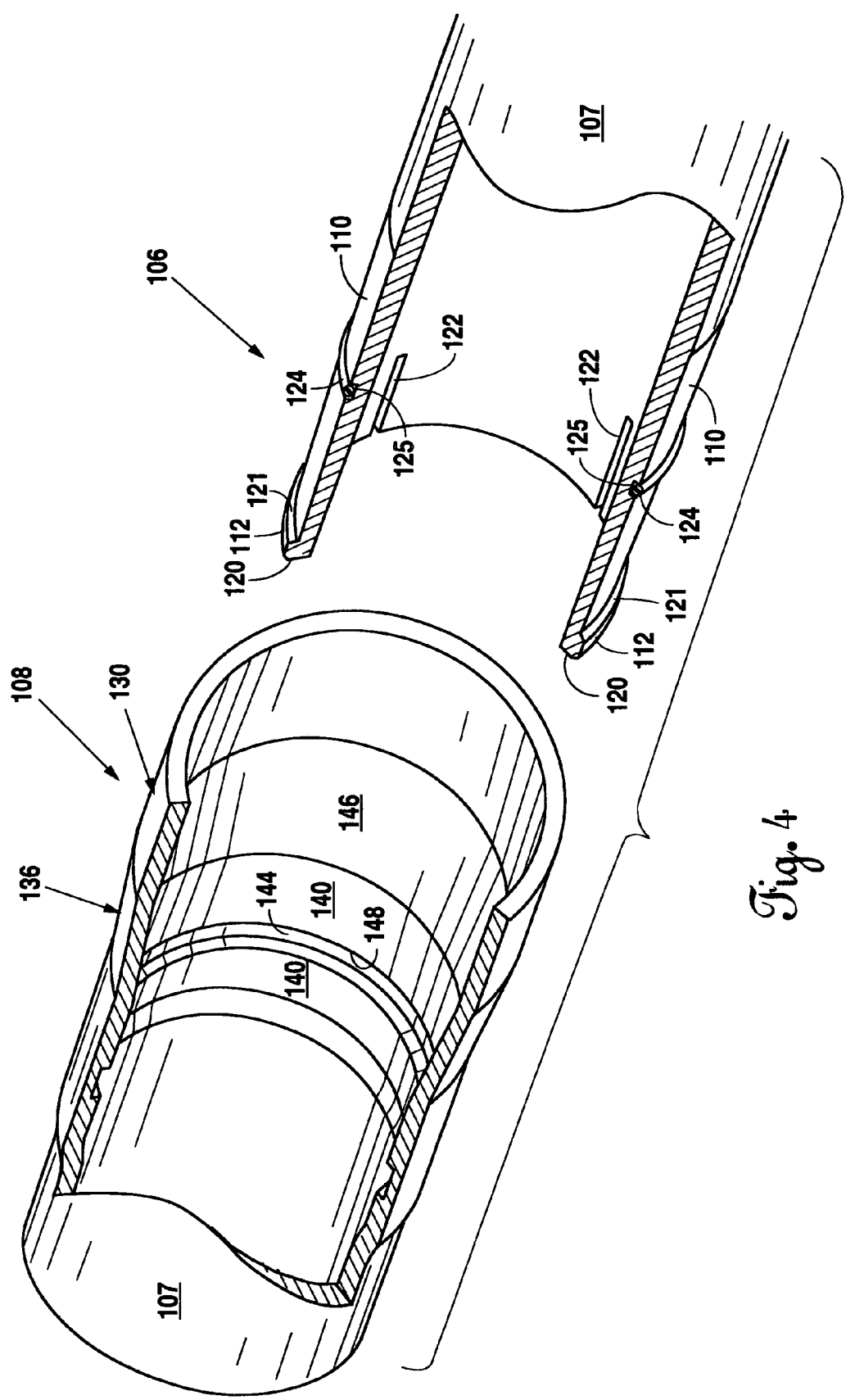
FIG. 4 is a perspective cutaway view of the male end and female end of the present invention.

FIGS. 2 and 3 show a side view and cross sectional view of the female end 108 of the water well casing 102 of the present invention while FIG. 4 illustrates a cutaway view. As shown in these views, the female end 108 has varying interior diameter which is wider at its outermost end. A first female section 130 is located at the outermost end of female end 108. The first female section 130 has a widened interior diameter 132 sufficient to receive the male end 106 and lip 112 of a similar casing with minimal clearance.

In the preferred embodiment, the length of the first female section 130 is sufficient to allow the first female section 130 to act as an alignment sleeve for the male end 106 of a similar casing. However, it is anticipated that the first female section 130 could be of varying lengths or have no length and only be the mouth of the female end 108. Also, in the preferred embodiment, the thickness of the wall of the first female section 130 is substantially equal to the thickness of the wall of the main length 107, such that, the outer diameter 134 of the first female section 130 is also widened. However, it is anticipated that the thickness of the first female section 130 and thus, its outer diameter 134 could vary.

Still referring to FIGS. 2, 3, and 4, a second female section 136 extends inwardly from the first female section 130. The second female section 136 has a tapering interior diameter 137 which narrows from the widened interior diameter 132 of the first female section 130 to a diameter which is less than the outer diameter of the lip 112 at the leading edge of the male end 106. In the preferred embodiment, the thickness of the wall of the second female section 136 is substantially equal to the thickness of the wall of the main length 107, such that, the outer diameter of the second female section 136 also tapers and narrows. However, it is anticipated that the thickness of the second female section 136 and thus, its outer diameter could vary.

Still referring to FIGS. 2, 3, and 4, a third female section 140 extends inwardly from the inner most end of the second female section 136 and has an interior diameter 142 which is substantially equal to the narrowest diameter of the tapering second female section 136. In the preferred embodiment, the thickness of the wall of the third female section 140 is substantially equal to the thickness of the wall of the main length 107. However, it is anticipated that the thickness of the third female section 140, and thus, its outer diameter could vary.

Figure 5:
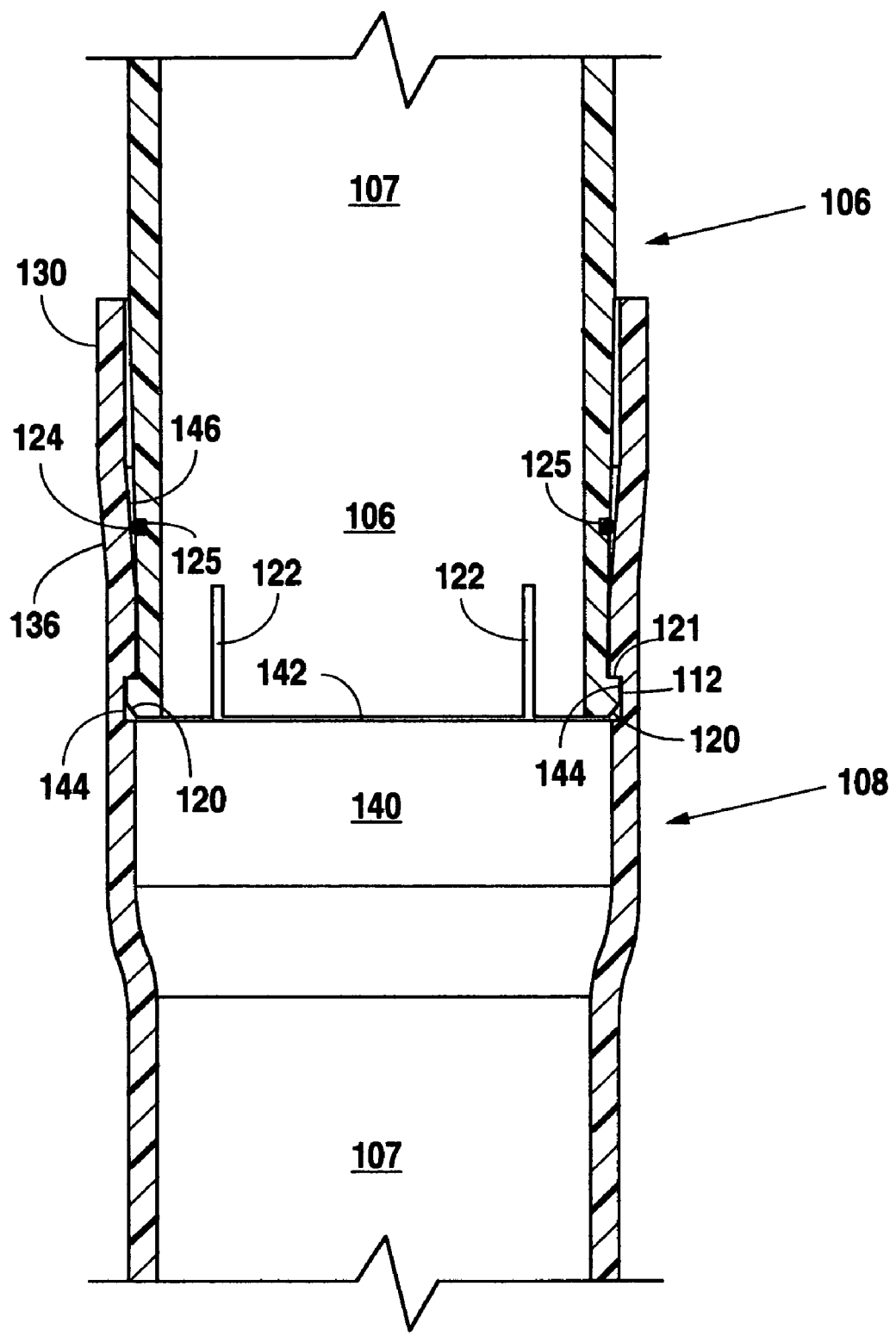
FIG. 5 is a cross-section view of FIG. 1 along cutting plane 5-5 of male end and female end.

Referring to FIGS. 3, 4, and 5, a circumferential groove 144 is cut into the interior surface of the female end 108. The groove 144 is of sufficient width and depth to receive the lip 112 at the leading edge of the male end 106 of a similar casing. In the preferred embodiment, the groove is positioned in the third female section 140. However, it is anticipated that the groove could also be positioned in the second female section 136.

As shown in FIGS. 2, 3, 4, and 5, an O-ring 124 is placed around the circumference of and engages the male end 106 of the casing 102. In the preferred embodiment, the O-ring rests within a groove 125 cut into the outer surface of the male end 106 around its circumference. However, it is anticipated that other placements of the O-ring could be utilized.

FIG. 4 depicts the general placement of a male end 106 and a female end 108 prior to insertion of male end 106 into female end 108. FIG. 5 is a cross-section view of the water well casing 102 with the male end 106 fully inserted into the female end 108.

Referring to FIGS. 4 and 5, in the preferred embodiment, as the male end 106 of casing 102 is inserted into the female end 108, the outer diameter of the lip 112 at the male end 106 makes contact with the interior surface 146 of the tapered second female section 136. As the male end 106 is further inserted, the interior surface 146 of the second female section 136 exerts a compressive force onto the lip 112 resulting in compression of the male end 106 with narrowing of the slots 122. At full insertion of the male end 106 into the female end 108, the lip 112 reaches groove 144 of female end 108, the compressive force on the lip 112 is released and the lip 112 expands into groove 144. The squared shoulder 121 engages the front wall 148 of the groove 144 locking the male end 106 of the lip 112 into female end 108. The engagement of the squared shoulder 121 of the lip 112 with the front wall 148 of the groove 144 resists pulling forces and prevents the connected casing 102 from being pulled apart under the hanging loads which exist when the casing 102 is placed in the water well. In addition, at full insertion, the O-ring 124 on male end 106 makes contact with the interior surface of female end 108, creating a seal.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A single piece polyvinyl chloride (PVC) well casing comprising:

a cylindrical main length extending between a cylindrical male end and a cylindrical female end, said cylindrical main length having uniform interior and exterior diameters;

said male end having at least one slot through the wall of said casing at the leading edge of said male end, said slot allowing said leading edge of said male end to radially compress a lip at said leading edge of said male end;

said female end having a first widened interior diameter at its outermost end wherein said first widened interior diameter is sufficient to receive a male end and a lip of a similar length of well casing with minimal clearance;

said interior diameter of said female end tapering from said first widened interior diameter to a second widened interior diameter;

said second widened interior diameter being less than the exterior diameter of said male end and said lip of said similar length of well casing;

a first groove on the interior surface of said female end, said groove positioned to and having sufficient width to receive said lip of said similar length of well casing therein.

2. The single piece polyvinyl chloride (PVC) well casing recited in claim 1 further comprising an O-ring around the circumference of said male end.

3. The single piece polyvinyl chloride (PVC) well casing recited in claim 2 further comprising a second groove on the outer surface of said male end positioned to receive said O-ring therein.

4. The single piece polyvinyl chloride (PVC) well casing recited in claim 1 wherein said first groove is entirely within the width of the wall of said casing.

5. The single piece polyvinyl chloride (PVC) well casing recited in claim 1 wherein the interior diameter of said male end is substantially equal to said interior diameter of said main length.

6. The single piece polyvinyl chloride (PVC) well casing recited in claim 5 wherein the exterior diameter of said male end tapers from said main length to said lip.

7. The single piece polyvinyl chloride (PVC) well casing recited in claim 1 wherein said at least one slot is a plurality of slots spaced around the circumference of said male end.

8. The single piece polyvinyl chloride (PVC) well casing recited in claim 7 wherein the said plurality of slots are evenly spaced around the circumference of said male end.

9. The single piece polyvinyl chloride (PVC) well casing recited in claim 1 wherein said lip is beveled at said lip's leading edge.

10. The single piece polyvinyl chloride (PVC) well casing recited in claim 9 wherein said lip forms a shoulder at said lip's nonleading edge.

11. The single piece of polyvinyl chloride (PVC) well casing recited in claim 1 wherein said lip extends radially outwardly from said leading edge of said male end.

12. The single piece of polyvinyl chloride (PVC) well casing recited in claim 1 wherein said lip extends from the entire leading edge of said male end.

13. The single piece of polyvinyl chloride (PVC) well casing recited in claim 1 wherein said first groove is recessed in the interior surface of said female end.

14. The single piece of polyvinyl chloride (PVC) well casing recited in claims 1 or 13 wherein said first groove extends around substantially the entire circumference of said interior surface of said female end.

* * * * *